(12) United States Patent
Ikeno et al.

(10) Patent No.: US 6,818,785 B2
(45) Date of Patent: Nov. 16, 2004

(54) METHOD FOR PURIFYING FLUOROARYL BORANE DERIVATIVE AND BIS (FLUORARYL) BORANE DERIVATIVE

(75) Inventors: Ikuyo Ikeno, Osaka (JP); Hitoshi Mitsui, Kitakatsuragi-gun (JP); Toshiya Iida, Suita (JP); Toshimitsu Moriguchi, Takatsuki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/220,635
(22) PCT Filed: Dec. 10, 2001
(86) PCT No.: PCT/JP01/10791
§ 371 (c)(1),
(2), (4) Date: Sep. 4, 2002
(87) PCT Pub. No.: WO02/48156
PCT Pub. Date: Jun. 20, 2002

(65) Prior Publication Data
US 2003/0050282 A1 Mar. 13, 2003

(30) Foreign Application Priority Data
Dec. 11, 2000 (JP) .................................... 2000-376612

(51) Int. Cl.⁷ .............................. C07F 5/04; C07F 5/02
(52) U.S. Cl. ........................................... 558/298; 562/7
(58) Field of Search .............................. 562/7; 558/286, 558/298

(56) References Cited
U.S. PATENT DOCUMENTS
5,272,236 A  12/1993  Lai et al.

FOREIGN PATENT DOCUMENTS

| | | |
|---|---|---|
| DE | 100 59 717 A1 * | 9/2001 |
| FR | 2071171 * | 10/1979 |
| JP | 10-54828 | 2/1998 |
| WO | 00/37476 A1 | 6/2000 |

OTHER PUBLICATIONS

CA:130:81252 abstract of Synett by Ishihara et al (5) pp 597–599 1997.*
CA:127:293341 abs of Organometallics by Duchateau et al 16(23) pp 4995–5005 1997.*
CA:63:89010 abs of Chemische Berichte by Niedenzu et al 98(9) pp 3050–3052 1965.*
CA:127:108855 abs of WO 9720815 Jun. 1997.*
CA:94:102952 abs of Journal of Organic Chemistry by Ladd 46(1) pp 203–206 1981.*
"Polyfluoraryl Organometallic Compounds. Part II. Pentafluorophenylboron Halides and Some Derived Compounds" (R.D. Chambers et al., J.Chem.Soc. (1965) pp3933–3939).
"Borane–functionalized Oxide Supports: Development of Active Supported Metallocene Catalysts at Low Aluminoxane Loading" (Jun Tian et al., Journal of Molecular Catalysis A: Chemical 144(1999) pp 137–150).

* cited by examiner

Primary Examiner—Jean F. Vollano
(74) Attorney, Agent, or Firm—Nixon & Vanderhye P.C.

(57) ABSTRACT

After a fluoroaryl borane derivative is precipitated from a solution containing the fluoroaryl borane derivative, a bis (fluoroaryl) borane derivative, and a hydrocarbon solvent and is subjected to first filtration so that the fluoroaryl borane derivative is isolated, a filtrate that has been obtained by the first filtration is cooled and the bis (fluoroaryl) borane derivative is separated and is subjected to second filtration so that the bis (fluoroaryl) borane derivative is isolated. In a case where the solution contains fluorobenzene, the solution is concentrated, so that the fluorobenzene is removed. Thus, it is possible to provide the high-purity fluoroaryl borane derivative and bis (fluoroaryl) borane derivative having no impurity with ease and at a low cost.

5 Claims, No Drawings

METHOD FOR PURIFYING FLUOROARYL BORANE DERIVATIVE AND BIS (FLUORARYL) BORANE DERIVATIVE

This application is the U.S. national phase of international application PCT/JP01/17091 filed 10 Dec. 2001, which designated the U.S.

TECHNICAL FIELD

The present invention relates to a method for producing a fluoroaryl borane derivative and a bis (fluoroaryl) borane derivative such as a pentafluorophenyl boronic acid and a bis (pentafluorophenyl) borinic acid, which are useful as a polymerization catalyst, a polymerization co-catalyst, a catalyst for photopolymerization of silicone, an intermediate thereof, and an intermediate of a medicine or an agricultural chemical, for example.

BACKGROUND ART

Fluoroaryl borane derivatives and bis (fluoroaryl) borane derivatives such as pentafluorophenyl boronic acid and bis (pentafluorophenyl) borinic acid, are compounds useful as polymerization catalysts, polymerization co-catalysts, catalysts for photopolymerization of silicone, intermediates thereof, and intermediates of medicines or agricultural chemicals, for example.

For instance, as a manufacturing method of pentafluorophenyl boronic acid, J. Chem. Soc (1965) 3933–3939 discloses a method in which dichloropentafluorophenyl borane is added to acetone/water solution at a temperature of −78° C., then the acetone solution is concentrated, so that the pentafluorophenyl boronic acid is sublimated for purification, so as to be isolated. Further, as a manufacturing method of bis (pentafluorophenyl) borinic acid, it discloses a method in which a solution of bis (pentafluorophenyl) chloro borane in acetone is added to acetone/water solution at a temperature of −20° C., then the acetone solution is concentrated, so that the bis (pentafluorophenyl) borinic acid is sublimated for purification, so as to be isolated. Furthermore, the dichloropentafluorophenyl borane which is a precursor of pentafluorophenyl boronic acid, and the bis (pentafluorophenyl) chloro borane, which is a precursor of bis (pentafluorophenyl) borinic acid are synthesized by reacting pentafluorophenyl trimethyl tin or bis (pentafluorophenyl) dimethyl tin with boron trichloride. Upon synthesizing the dichloropentafluorophenyl borane, trimethyl tin chloride is produced as a by-product, and upon synthesizing the bis (pentafluorophenyl) chloro borane, dimethyl tin dichloride is produced as a by-product. However, it is difficult to purify dichloropentafluorophenyl borane and bis (pentafluorophenyl) chloro borane by distillation for the following reason: when these reaction mixtures are distilled so as to purify dichloropentafluorophenyl borane and bis (pentafluorophenyl) chloro borane as objects, trimethyl tin chloride reacts with an excess of boron trichloride so as to produce dimethyl tin dichloride which is identical to the by-product produced upon synthesizing bis (pentafluorophenyl) chloro borane, so that the dimethyl tin dichrolide is sublimed. Thus, it is difficult to purify dichloropentafluorophenyl borane and bis (pentafluorophenyl) chloro borane with high yield.

Moreover, J. Molecular Catalysis A: Chemical 144 (1999) 137–150 and WO 0037376 (2000) disclose that bis (pentafluorophenyl) borinic acid is prepared by heating a tris (pentafluorophenyl) borane hydrate.

However, the method disclosed in the above-mentioned J. Molecular Catalysis A: Chemical 144 (1999) 137–150 discloses only how to manufacture bis (pentafluorophenyl) borinic acid, and fails to recite how to isolate bis (pentafluorophenyl) borinic acid from a reaction mixture.

J. Molecular Catalysis A: Chemical 144 (1999) 137–150 recites only that it was confirmed by $^{19}$F-NMR that bis (pentafluorophenyl) borinic acid was prepared by adding water to a toluene-d8 solution of tris (pentafluorophenyl) borane so as to prepare a tris (pentafluorophenyl) borane hydrate, then heating the solution of the tris (pentafluorophenyl) borane hydrate.

Moreover, WO 0037476 (2000) discloses preparation of bis (pentafluorophenyl) borinic acid by heating a tris (pentafluorophenyl) borane hydrate, and an isolation method of bis (pentafluorophenyl) borinic acid. Specifically, a toluene solution of tris (pentafluorophenyl) borane is heated up to 100° C. Then, to the solution, a toluene solution containing 2.5 equivalent amount of water is dropped so that reaction carried out at 100° C. After finishing the reaction, the reaction mixture is dried in vacuo so as to isolate bis (pentafluorophenyl) borinic acid. However, it is recited that the bis (pentafluorophenyl) borinic acid obtained by this method contains boroxine by 5% as impurities. In short, this method has such a problem that the isolated bis (pentafluorophenyl) borinic acid has a low purity.

Moreover, that patent also discloses a method in which alminium sulfate 18 hydrate is used instead of water. Specifically, aluminium sulfate 18 hydrate is added to a toluene solution of tris (pentafluorophenyl) borane. After the solution is refluxed, insoluble alminium sulfate is separated from the reaction mixture. A solvent of a filtrate is removed in vacuo. Toluene is added to the thus obtained residue. After stirring, the insoluble matter passes through a G4 sintered-glass so as to be separated. The solvent of the filtrate is again removed in vacuo. Heptane is added to the residue. The solution is stirred and filtered so that a cake is obtained. Finally, the thus obtained cake is washed with heptane, and dried in vacuo so as to isolate bis (pentafluorophenyl) borinic acid. However, this method has such a problem that it is necessary to remove the by-product alminium sulfate and its process is so complicated.

As described above, the prior methods have many problems to be improved. Although conditions of reduced pressure etc. are unexplained, boroxine is generated as impurity. Thus, in the case where the bis (fluoroaryl) borane derivative containing impurities is used as polymerization catalyst for example, there occur such problems that polymerization activity declines, etc.

Therefore, for industrial application of a fluoroaryl borane derivative and a bis (fluoroaryl) borane derivative, such as pentafluorophenyl boronic acid and bis (pentafluorophenyl) borinic acid, as catalysts or the like, there is a desire for a method by which the highly-purified fluoroaryl borane derivative and bis (fluoroaryl) borane derivative are easily isolated from a reaction mixture, and highly purified. Thus, the present invention, which is contrived in view of the foregoing problems, has an object of providing a method by which a fluoroaryl borane derivative and a bis (fluoroaryl) borane derivative can be produced, isolated, and highly purified with ease.

DISCLOSURE OF INVENTION

The present invention, in order to attain the above-mentioned object, carried out intensive studies on a method for purifying a fluoroaryl borane derivative and a bis (fluoroaryl) borane derivative, especially on a condition for filtrating, a condition for purifying, and the like. As a result, they found a method for purifying by which it is possible to readily separate the fluoroaryl borane derivative and the bis (fluoroaryl) borane derivative respectively as desired. Furthermore, they found a method for obtaining such an object that the content of a specific compound contained in the fluoroaryl borane derivative or the bis (fluoroaryl) borane derivative as impurities is not more than a specific amount, thus completing the present invention.

Compared with the prior arts, the fluoroaryl borane derivative and the bis (fluoroaryl) borane derivative obtained by the foregoing method for purifying are highly purified, so that it is possible to preferably use them as polymerization catalysts having high polymerization activity.

That is, in order to solve the foregoing problems, a method of the present invention for purifying a fluoroaryl borane derivative and a bis (fluoroaryl) borane derivative includes the steps of: precipitating the fluoroaryl borane derivative from a solution containing a fluoroaryl borane derivative, a bis (fluoroaryl) borane derivative, and a hydrocarbon solvent; performing first filtration; cooling a filtrate that has been obtained by the first filtration; precipitating the bis (fluoroaryl) borane derivative from the filtrate; and performing second filtration, and the fluoroaryl borane derivative is represented by General Formula (1):

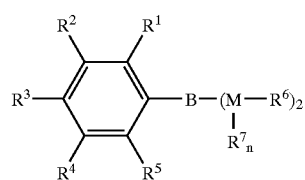

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents a hydrogen atom or a hydrocarbon group, and M represents an atom belonging to Group 5B or Group 6B, and n represents 0 or 1), and the bis (fluoroaryl) borane derivative is represented by General Formula (2):

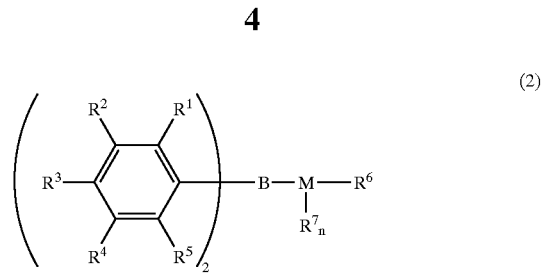

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents a hydrogen atom or a hydrocarbon group, and M represents an atom belonging to Group 5B or Group 6B, and n represents 0 or 1).

According to the arrangement, it is possible to purify the fluoroaryl borane derivative and the bis (fluoroaryl) borane derivative from a solution containing the fluoroaryl borane derivative, the bis (fluoroaryl) borane derivative, and the hydrocarbon solvent with ease and at a low cost.

That is, since the solubility of bis (fluoroaryl) borane derivative with respect to the hydrocarbon solvent is higher than that of the fluoroaryl borane derivative and they are greatly different from each other, it is possible to selectively precipitate only the fluoroaryl borane derivative without precipitating the bis (fluoroaryl) borane derivative from the solution containing the fluoroaryl borane derivative, the bis (fluoroaryl) borane derivative, and the hydrocarbon solvent within a range of a specific temperature.

Thus, the solution is set to be in the range of a specific temperature, so that it is possible to selectively precipitate only the fluoroaryl borane derivative from the solution. Since the deposit precipitated from the solution can be readily isolated by filtration, the first filtration enables the fluoroaryl borane derivative to be isolated from the solution with ease.

That is, since the solubility of bis (fluoroaryl) borane derivative with respect to the hydrocarbon solvent is higher than that of the fluoroaryl borane derivative, almost all or all the deposit precipitated at a specific temperature range is the fluoroaryl borane derivative, almost all or all the bis (fluoroaryl) borane derivative dissolves in the filtrate that has been obtained by the first filtration. Since the solubility of bis (fluoroaryl) borane derivative declines corresponding to a decline in a temperature, it is possible to precipitate the bis (fluoroaryl) borane derivative that has dissolved in the filtrate by cooling the filtrate.

In this manner, after the fluoroaryl borane derivative is isolated from the solution by the first filtration, a crystal of the bis (fluoroaryl) borane derivative is precipitated from the filtrate as a deposit, so that the bis (fluoroaryl) borane derivative can be isolated as a solid by the second filtration.

Thus, it is possible to isolate the fluoroaryl borane derivative and the bis (fluoroaryl) borane derivative respectively from the solution containing the fluoroaryl borane derivative, the bis (fluoroaryl) borane derivative, and the hydrocarbon solvent. Namely, it is possible to purify the fluoroaryl borane derivative and the bis (fluoroaryl) borane derivative respectively.

Therefore, according to the method of the present invention for purifying, it is possible to readily isolate and purify the fluoroaryl borane derivative and the bis (fluoroaryl) borane derivative from the reaction solvent containing the fluoroaryl borane derivative and the bis (fluoroaryl) borane derivative without including industrially undesirable steps such as drying up the solvent. That is, according to the method of the present invention for purifying, it is possible to purify the fluoroaryl borane derivative and the bis (fluoroaryl) borane derivative respectively so as to enable them to be used as a catalyst etc. industrially.

In order to solve the foregoing problems, a method of the present invention for purifying a fluoroaryl borane derivative and a bis (fluoroaryl) borane derivative includes the steps of: precipitating the fluoroaryl borane derivative from a solution containing the fluoroaryl borane derivative, the bis (fluoroaryl) borane derivative, fluorobenzene, and a hydrocarbon solvent; performing first filtration so that the fluoroaryl borane derivative is isolated; precipitating the bis (fluoroaryl) borane derivative from a filtrate that has been obtained by the first filtration; and performing second filtration so that the bis (fluoroaryl) borane derivative is isolated as a solid, and the fluoroaryl borane derivative is represented by General Formula (1):

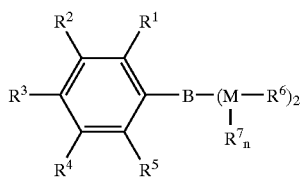

(1)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), and the bis (fluoroaryl) borane derivative is represented by General Formula (2):

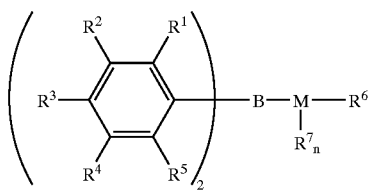

(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ representing the fluorine atom, and each of $R^6$ and $R^7$ independently represents one of a hydrogen atom and a hydrocarbon group, and M represents an atom belonging to Group 5B or Group 6B, and n represents 0 or 1), and the fluorobenzene is represented by General Formula (3):

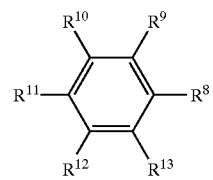

(3)

(where each of $R^9$, $R^{10}$, $R^{11}$, $R^{12}$, and $R^{13}$ independently represents one of a hydrogen atom, a fluorine atom, a hydrocarbon group, and an alkoxy group, and at least one of $R^9$, $R^{10}$, $R^{11}$, $R^{12}$, and $R^{13}$ represents the fluorine atom, $R^8$ represents one of a hydrogen atom and a hydrocarbon group).

According to the arrangement, it is possible to readily isolate and purify the fluoroaryl borane derivative and the bis (fluoroaryl) borane derivative respectively as solids from the solution containing the fluoroaryl borane derivative, the bis (fluoroaryl) borane derivative, the fluorobenzene, and the hydrocarbon solvent.

That is, the fluoroaryl borane derivative obtained by the first filtration is isolated from the solution containing the fluoroaryl borane derivative, the bis (fluoroaryl) borane derivative, the fluorobenzene, and the hydrocarbon solvent, and the filtrate is cooled so as to precipitate the bis (fluoroaryl) borane derivative, then the second filtration is performed, so that it is possible to isolate the bis (fluoroaryl) borane derivative as a solid.

Thus, it is possible to isolate the fluoroaryl borane derivative and the bis (fluoroaryl) borane derivative respectively from the solution containing the fluoroaryl borane derivative, the bis (fluoroaryl) borane derivative, the fluorobenzene, and the hydrocarbon solvent. Namely, it is possible to purify the fluoroaryl borane derivative and the bis (fluoroaryl) borane derivative respectively from the solution.

Thus, according to the method of the present invention for purifying, it is possible to readily purify the fluoroaryl borane derivative and the bis (fluoroaryl) borane derivative respectively from the reaction mixture containing the fluoroaryl borane derivative, the bis (fluoroaryl) borane derivative, and the fluorobenzene. That is, according to the method of the present invention for purifying, it is possible to purify the fluoroaryl borane derivative and the bis (fluoroaryl) borane derivative so as to industrially use them as catalysts.

In order to solve the foregoing problems, a method of the present invention for purifying the fluoroaryl borane derivative and the bis (fluoroaryl) borane derivative includes the steps of: concentrating a solution containing the fluoroaryl borane derivative, the bis (fluoroaryl) borane derivative, fluorobenzene, and a hydrocarbon solvent so as to remove the fluorobenzene from the solution; precipitating, the fluoroaryl borane derivative; performing first filtration; cooling a filtrate that has been obtained by the first filtration; precipitating the bis (fluoroaryl) borane derivative; and performing second filtration, and the fluoroaryl borane derivative is represented by General Formula (1):

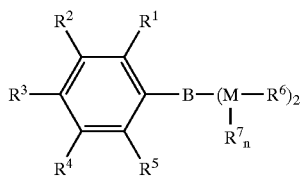

(1)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), and the bis (fluoroaryl) borane derivative is represented by General Formula (2):

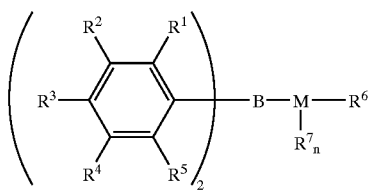

(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), and the fluorobenzene is represented by General Formula (3):

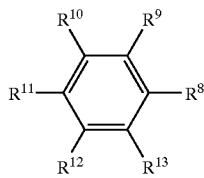

(3)

(where each of $R^9$, $R^{10}$, $R^{11}$, $R^{12}$, and $R^{13}$ independently represents one of a hydrogen atom, a fluorine atom, a hydrocarbon group, and an alkoxy group, and at least one of $R^9$, $R^{10}$, $R^{11}$, $R^{12}$, and $R^{13}$ representing the fluorine atom, and $R^8$ represents one of a hydrogen atom and a hydrocarbon group).

According to the arrangement, it is possible to isolate the fluoroaryl borane derivative and the bis (fluoroaryl) borane derivative as solids from the solution containing the fluoroaryl borane derivative, the bis (fluoroaryl) borane derivative, the fluorobenzene, and the hydrocarbon solvent with ease, so as to purify them.

That is, it is possible to remove the fluorobenzene from the solution as distillate by concentrating the solution con taining the fluoroaryl borane derivative and the bis (fluoroaryl) borane derivative, the fluorobenzene, and the hydrocarbon solvent. Next, the fluoroaryl borane derivative is isolated from the concentrated solution that has been obtained by the first filtration, then the filtrate is cooled so as to separate the bis (fluoroaryl) borane derivative, so that the bis (fluoroaryl) borane derivative can be isolated as a solid by performing the second flirtation.

Thus, it is possible to isolate the fluoroaryl borane derivative and the bis (fluoroaryl) borane derivative respectively from the solution containing the fluoroaryl borane derivative, the bis (fluoroaryl) borane derivative, the fluorobenzene, and the hydrocarbon solvent. Namely, it is possible to purify the fluoroaryl borane derivative and the bis (fluoroaryl) borane derivative respectively.

Therefore, according to the method of the present invention for purifying, it is possible to readily purify the fluoroaryl borane derivative and the bis (fluoroaryl) borane derivative respectively from the solution containing the fluoroaryl borane derivative, the bis (fluoroaryl) borane derivative, the fluorobenzene, and the hydrocarbon solvent. That is, according to the method of the present invention for purifying, it is possible to purify the fluoroaryl borane derivative and the bis (fluoroaryl) borane derivative respectively so as to industrially use them as catalysts.

In order to solve the foregoing problems, a method of the present invention for purifying a fluoroaryl borane derivative and a bis (fluoroaryl) borane derivative includes the steps of: precipitating the fluoroaryl borane derivative from a solution containing the fluoroaryl borane derivative, the bis (fluoroaryl) borane derivative, fluorobenzene, and a hydrocarbon solvent; performing first filtration; concentrating a filtrate that has been obtained by the first filtration so as to remove the fluorobenzene from the solution; precipitating the bis (fluoroaryl) borane derivative from the filtrate; and performing second filtration, and the fluoroaryl borane derivative is represented by General Formula (1):

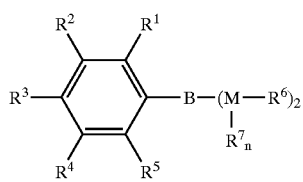

(1)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), and the bis (fluoroaryl) borane derivative is represented by General Formula (2):

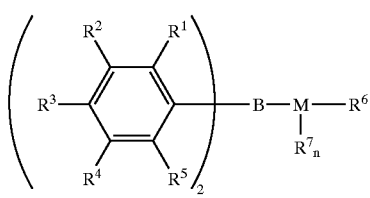

(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), and the fluorobenzene is represented by General Formula (3):

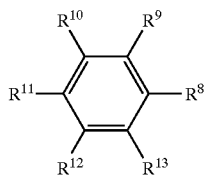

(3)

(where each of $R^9$, $R^{10}$, $R^{11}$, $R^{12}$, and $R^{13}$ independently represents one of a hydrogen atom, a fluorine atom, a hydrocarbon group, and an alkoxy group, and at least one of $R^9$, $R^{10}$, $R^{11}$, $R^{12}$, and $R^{13}$ represents the fluorine atom, and $R^8$ represents one of a hydrogen atom and a hydrocarbon group).

According to the arrangement, it is possible to readily isolate the fluoroaryl borane derivative and the bis (fluoroaryl) borane derivative respectively from the solution containing the fluoroaryl borane derivative, the bis (fluoroaryl) borane derivative, the fluorobenzene, and the hydrocarbon solvent so as to purify them.

That is, after the fluoroaryl borane derivative is isolated as a solid by performing the first filtration, the filtrate is concentrated, so that it is possible to remove the fluorobenzene from the solution as distillate by concentrating the solution containing the fluoroaryl borane derivative, fluorobenzene, the bis (fluoroaryl) borane derivative, and the hydrocarbon solvent. Next, the fluoroaryl borane derivative is isolated from the concentrated solution that has been obtained by the first filtration, then the filtrate is cooled as required so as to precipitate the bis (fluoroaryl) borane derivative, so that the bis (fluoroaryl) borane derivative can be isolated as a solid by performing the second flirtation.

Thus, it is possible to isolate the fluoroaryl borane derivative and the bis (fluoroaryl) borane derivative as solids respectively from the solution containing the fluoroaryl borane derivative, the bis (fluoroaryl) borane derivative, the fluorobenzene, and the hydrocarbon solvent. Namely, it is possible to purify the fluoroaryl borane derivative and the bis (fluoroaryl) borane derivative respectively.

Therefore, according to the method of the present invention for purifying, it is possible to readily purify the fluoroaryl borane derivative and the bis (fluoroaryl) borane derivative respectively from the solution containing the fluoroaryl borane derivative, the bis (fluoroaryl) borane derivative, the fluorobenzene, and the hydrocarbon solvent. That is, according to the method of the present invention for purifying, it is possible to purify the fluoroaryl borane derivative and the bis (fluoroaryl) borane derivative respectively so as to industrially use them as catalysts. P In order to solve the foregoing problems, a method of the present invention for purifying the fluoroaryl borane derivative and the bis (fluoroaryl) borane derivative is arranged so that a solution containing the fluoroaryl borane derivative and the bis (fluoroaryl) borane derivative is obtained by reacting iris (fluoroaryl) borane with a compound represented by General Formula (5) in a molar ratio from 1:1.9 to 1:5 in a hydrocarbon solvent, and the tris (fluoroaryl) borane is represented by General Formula (4):

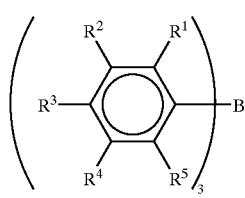

(4)

(where each $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom), and the compound is represented by General Formula (5):

$$R^6\text{—}MR^{14}(R^7)n \qquad (5)$$

(where each of $R^6$, $R^7$, and $R^{14}$ independently represents one of a hydrogen atom and a hydrocarbon group, and M represents an atom belonging to Group 15 or Group 16 and n represents 0 or 1).

According to the arrangement, it is possible to selectively obtain the fluoroaryl borane derivative by reacting the tris (fluoroaryl) borane with the compound represented by General Formula (5) in the hydrocarbon solvent. That is, it is possible to selectively obtain the fluoroaryl borane derivative by reacting the tris (fluoroaryl) borane with the compound represented by General Formula (5) in a molar ratio from 1:1.9 to 1:5 in the hydrocarbon solvent.

Therefore, according to the reaction, it is possible to obtain the solution containing much fluoroaryl borane derivative as the solution containing the fluoroaryl borane derivative and the bis (fluoroaryl) borane derivative. After the fluoroaryl borane derivative is isolated from the solution by the first filtration, a crystal of the bis (fluoroaryl) borane derivative is separated from the filtrate as a precipitated deposit, so that it is possible to isolate the bis (fluoroaryl) borane derivative as a solid by the second filtration. Furthermore, since the solution contains a large quantity of fluoroaryl borane derivative, it is possible to isolate the fluoroaryl borane derivative efficiently.

Thus, it is possible to obtain the solution containing much fluoroaryl borane derivative as a solution containing the fluoroaryl borane derivative and the bis (fluoroaryl) borane derivative, so that it is possible to isolate the fluoroaryl borane derivative and the bis (fluoroaryl) borane derivative respectively, that is, it is possible to purify the fluoroaryl borane derivative and the bis (fluoroaryl) borane derivative respectively. Moreover, it is possible to obtain the fluoroaryl borane derivative with a high isolation yield.

Thus, according to the method of the present invention for purifying, it is possible to readily isolate and purify the fluoroaryl borane derivative and the bis (fluoroaryl) borane derivative respectively from the reaction mixture containing the fluoroaryl borane derivative and the bis (fluoroaryl) borane derivative without including industrially undesirable steps such as drying up the solvent. Moreover, it is possible to obtain the fluoroaryl borane derivative with a high isolation yield. That is, according to the method of the present invention for purifying, it is possible to purify the fluoroaryl borane derivative and the bis (fluoroaryl) borane derivative respectively so as to enable the fluoroaryl borane derivative in particular to be used as a catalyst etc. industrially.

In order to solve the foregoing problems, a method of the present invention for purifying the fluoroaryl borane derivative and the bis (fluoroaryl) borane derivative is arranged so that a solution containing the fluoroaryl borane derivative and the bis (fluoroaryl) borane derivative is obtained by reacting tris (fluoroaryl) borane with a compound represented by General Formula (5) in a molar ratio from 1:0.9 to 1:1.1 in a hydrocarbon solvent, and the iris (fluoroaryl) borane is represented by General Formula (4):

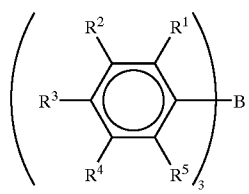

(4)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom), and the compound is represented by General Formula (5):

$$R^6-MR^{14}(R^7)n \qquad (5)$$

(where each of $R^6$, $R^7$, and $R^{14}$ independently represents one of a hydrogen atom and a hydrocarbon group, and M represents an atom belonging to Group 15 or Group 16 and n represents 0 or 1).

According to the arrangement, it is possible to selectively obtain the bis (fluoroaryl) borane derivative by reacting the tris (fluoroaryl) borane with the compound (5) in the hydrocarbon solvent. That is, it is possible to selectively obtain the bis (fluoroaryl) borane derivative by reacting the tris (fluoroaryl) borane with the compound represented by General Formula (5) in a molar ration from 1:0.9 to 1:11 in the hydrocarbon solvent.

Therefore, according to the reaction, it is possible to obtain the solution containing a large quantity of bis (fluoroaryl) borane derivative as the solution containing fluoroaryl borane derivative and the bis (fluoroaryl) borane derivative. After the fluoroaryl borane derivative is isolated from the solution by the first filtration, a crystal of the bis (fluoroaryl) borane derivative is separated from the filtrate as a precipitated deposit, so that it is possible to isolate the bis (fluoroaryl) borane derivative as a solid by the second filtration. Furthermore, since the solution contains a large quantity of bis (fluoroaryl) borane derivative, it is possible to isolate the fluoroaryl borane derivative efficiently.

Thus, it is possible to obtain the solution containing a large quantity of bis (fluoroaryl) borane derivative as a solution containing the fluoroaryl borane derivative and the bis (fluoroaryl) borane derivative, so that it is possible to isolate the fluoroaryl borane derivative and the bis (fluoroaryl) borane derivative respectively, that is, it is possible to purify the fluoroaryl borane derivative and the bis (fluoroaryl) borane derivative respectively. Moreover, it is possible to obtain the fluoroaryl borane derivative with a highly isolated yield.

Thus, according to the method of the present invention for purifying, it is possible to readily isolate and purify the fluoroaryl borane derivative and the bis (fluoroaryl) borane derivative respectively from the reaction mixture containing the fluoroaryl borane derivative and the bis (fluoroaryl) borane derivative without including industrially undesirable steps such as drying up the solvent. Moreover, it is possible to obtain the bis (fluoroaryl) borane derivative with a highly isolated yield. That is, according to the method of the present invention for purifying, it is possible to purify the fluoroaryl borane derivative and the bis (fluoroaryl) borane derivative respectively so as to enable the bis (fluoroaryl) borane derivative in particular to be used as a catalyst etc. industrially.

In the method of the present invention for purifying the fluoroaryl borane derivative and the bis (fluoroaryl) borane derivative, it is preferable that the hydrocarbon solvent is substantially an aliphatic hydrocarbon solvent.

According to the arrangement, it is possible to increase the yield at which the fluoroaryl borane derivative and the bis (fluoroaryl) borane derivative are isolated.

That is, since the solubility of bis (fluoroaryl) borane derivative with respect to the aliphatic hydrocarbon solvent is low under a low temperature condition, it is possible to precipitate a large part of the bis (fluoroaryl) borane derivative in the filtrate in a case where the hydrocarbon solvent is the aliphatic hydrocarbon solvent. Thus, it is possible to obtain the bis (fluoroaryl) borane derivative with a high isolation yield by the second filtration.

A fluoroaryl borane derivative of the present invention is a solid represented by General Formula (1):

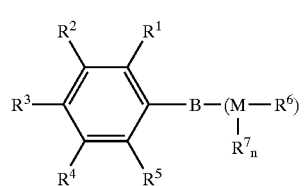

(1)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), wherein the fluoroaryl borane derivative contains a bis (fluoroaryl) borane derivative so that the content of the bis (fluoroaryl) borane is not more than 1% by weight, and the bis (fluoroaryl) borane derivative is represented by General Formula (2):

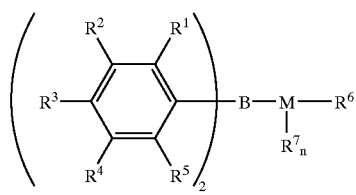

(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1).

It is preferable that purity of the fluoroaryl borane derivative is not less than 90%.

According to the arrangement, since the purity of the fluoroaryl borane derivative is high, it is possible to industrially use it more preferably as a catalyst.

A bis (fluoroaryl) borane derivative of the present invention is a solid represented by General Formula (2):

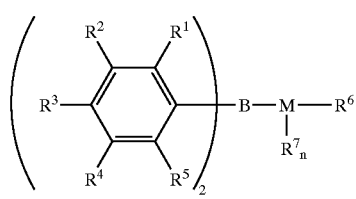

(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1), wherein the bis (fluoroaryl) borane derivative contains a fluoroaryl borane derivative so that the content of the fluoroaryl borane derivative is not, more than 1% by weight, and the bis (fluoroaryl) borane is represented by General Formula (2):

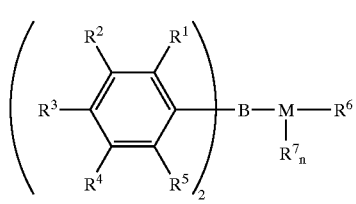

(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1).

It is preferable that purity of the bis (fluoroaryl) borane derivative is not less than 95%.

According to the arrangement, since the purity of the bis (fluoroaryl) borane derivative is high, it is possible to industrially use it more preferably as a catalyst.

In order to solve the foregoing problems, a method of the present invention for producing a fluoroaryl borane derivative includes the step of reacting tris (fluoroaryl) borane with a compound represented by General Formula (5) in a molar ratio from 1:1.9 to 1:5 in a hydrocarbon solvent, and the tris (fluoroaryl) borane is represented by General Formula (4):

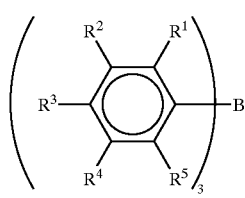

(4)

(where each of $R^1$, $R^2$, $R^3$, $R^4$, and $R^5$ independently represents one hydrogen atom, a fluorine atom, a hydrocarbon group, and an alkoxy group, and at one of $R^1$, $R^2$, $R^3$, $R^4$, and $R^5$ represents the fluorine atom), and the compound is represented by General Formula (5):

$$R^6-MR^{14}(R^7)n \qquad (5)$$

(where each of $R^6$, $R^7$, and $R^{14}$ independently represents one of a hydrogen atom and a hydrocarbon group, and M represents an atom belonging to Group 15 or Group 16, and n represents 0 or 1.

According to the arrangement, it is possible to selectively obtain the fluoroaryl borane derivative by reacting the tris (fluoroaryl) borane with the compound represented by General Formula (5) in the hydrocarbon solvent. That is, it is possible to selectively obtain the fluoroaryl borane derivative by reacting the tris (fluoroaryl) borane with the compound represented by General Formula (5) in a molar ratio from 1:1.9 to 1:5.0 in the hydrocarbon solvent.

In a method of the present invention for producing the fluoroaryl borane derivative, it is preferable that not more than 1 weight % bis (fluoroaryl) borane derivative is contained, and the bis (fluoroaryl) borane derivative is represented by General Formula (2):

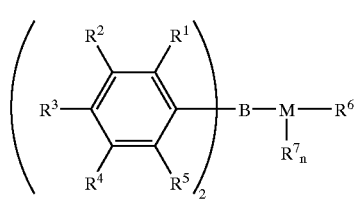

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1).

It is preferable that purity of the fluoroaryl borane derivative is not less than 90%.

According to the arrangement, since the purity of the fluoroaryl borane derivative is high, it is possible to industrially use it more preferably as a catalyst.

The following description will give fuller understanding of still another object, characteristic, and superiority of the present invention. Further, the benefit of the present invention will be clarified by the following description.

A method for producing a fluoroaryl borane derivative and a bis (fluoroaryl) borane derivative that should be purified by the method of the present invention for purifying is not particularly limited, but various methods can be employed. It is possible to produce the fluoroaryl borane derivative and the bis (fluoroaryl) borane derivative by reacting tris (fluoroaryl) borane with a compound represented by General Formula (5) in a hydrocarbon solvent, and the tris (fluoroaryl) borane is represented by General Formula (4):

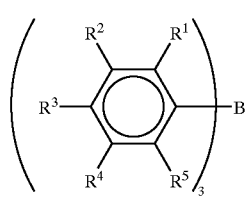

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom), and the compound is represented by General Formula (5):

$R^6$—$MR^{14}(R^7)n$ (5)

(where each of $R^6$, $R^7$, and $R^{14}$ independently represents one of a hydrogen atom and a hydrocarbon group, and M represents an atom belonging to Group 15 or Group 16, and n represents 0 or 1).

It is preferable to use such reaction that, for example, water is used as compound represented by General Formula (5) so as to hydrolyze the tris (fluoroaryl) borane. Note that, although it is possible to hydrolyze the tris (fluoroaryl) borane in the presence of hydrate such as aluminium sulfate 18 hydrate upon hydrolyzing, there occur such problems that: reaction process is complicated and it is required to remove generated salt such as aluminium sulfate. Thus, in the embodiments of the present invention, it is preferable to perform hydrolysis in the presence of water, and it is more preferable to perform the hydrolysis so that hydrate salt does not coexist. Here, the hydrolysis performed so that hydrate salt does not coexist is such that: an amount of hydrate salt which is allowed to exist is 0 to 5%, preferably 0 to 2%, and more preferably Oto 1%.

As methods for mixing the tris (fluoroaryl) borane and the compound represented by the General Formula (5) in the hydrocarbon solvent, for example, there are the following methods: the tris (fluoroaryl) borane is dissolved in the hydrocarbon solvent so as to make a solution, and the compound represented by General Formula (5) is added to the solution so as to be mixed, the tris (fluoroaryl) borane and the compound represented by General Formula (5) are added to and mixed in the hydrocarbon solvent at the same time, and (c) the tris (fluoroaryl) borane is added to and mixed in the hydrocarbon solvent in which the compound represented by General Formula (5) has been added.

A temperature at which the tris (fluoroaryl) borane and the compound represented by General Formula (5) are mixed in the hydrocarbon solvent preferably ranges from −100° C. to 300° C., and more preferably ranges from 0° C. to 200° C.

Note that, in the method for producing a fluoroaryl borane derivative and a bis (fluoroaryl) borane derivative that should be purified by the method for purifying according to the present invention, it is possible to selectively produce either the fluoroaryl borane derivative or the bis (fluoroaryl) borane derivative.

To obtain the fluoroaryl borane derivative represented by General Formula (1), for example, to obtain a pentafluorophenyl boronic acid etc. with high purity, the following reaction condition for obtaining the highly-purified fluoroaryl borane derivative represented by General Formula (1) and the method of the present invention for purifying are employed together, so that it is possible to selectively produce the pentafluorophenyl boronic acid as the fluoroaryl borane derivative represented by General Formula (1), more easily.

For example, in a case where water is used as the compound represented by General Formula (5) so as to perform hydrolysis while using the tris (pentafluorophenyl) borane as the tris (fluoroaryl) borane, water is used excessively with respect to the tris (pentafluorophenyl) borane, more specifically, the tris (pentafluorophenyl) borane and water are used in a molar ratio from 1:1.9 to 1:5.0, so that it is possible to selectively obtain the pentafluorophenyl boronic acid.

If the molar ratio of water with respect to the tris (fluoroaryl) borane is less than 1.9, more bis (fluoroaryl) borane derivative is generated, so that a yield of the fluoroaryl borane derivative decreases. Further, if the molar ratio of water with respect to the tris (fluoroaryl) borane is more than 5.0, reaction rate becomes extremely slow, so that this is industrially undesirable.

Contrary, to obtain the bis (fluoroaryl) borane derivative represented by General Formula (2), for example, to obtain a highly-purified bis (pentafluorophenyl) borinic acid etc., it is preferable that the following step is employed as a preceding step in combination with the method of the present invention for purifying.

The following reaction condition for obtaining the highly-purified bis (fluoroaryl) borane derivative represented by General Formula (2) and the method of the present invention for purifying are employed together, so that it is possible to selectively produce the bis (pentafluorophenyl) borinic acid as the bis (fluoroaryl) borane derivative represented by General Formula (2), more easily.

For example, in a case where water is used as the compound represented by General Formula (5) so as to perform hydrolysis while using the tris (pentafluorophenyl) borane as the tris (fluoroaryl) borane, the tris (pentafluorophenyl) borane and water are substantially equalized in a molar ratio, more specifically, the tris (pencafluorophenyl) borane and water are used in a molar ratio from 1:0.9 to 1:1.1, so that it is possible to selectively obtain the bis (pentafluorophenyl) borinic acid.

If the molar ratio of water with respect to the tris (fluoroaryl) borane is less than 0.9, a conversion of the tris (fluoroaryl) borane derivative decreases, so that a yield of the bis (fluoroaryl) borane derivative decreases. Further, if the molar ratio of water with respect to the tris (fluoroaryl) borane is more than 1.1, more fluoroaryl borane derivative is generated, so that the yield of the bis (fluoroaryl) borane derivative is low.

That is, to efficiently obtain the fluoroaryl borane derivative represented by General Formula (1), it is preferable that the tris (fluoroaryl) borane and the compound (5) are used in a molar ratio from 1:1.9 to 1:5.0. Further, to efficiently obtain the bis fluoroaryl borane derivative represented by General Formula (2), it is preferable that the tris (fluoroaryl) borane and the compound (5) are used in a molar ratio from 1:0.9 to 1:1.1.

In the present invention, it is preferable to employ the following producing method for selectively obtaining the fluoroaryl borane derivative represented by General Formula (1).

A method for producing a fluoroaryl borane derivative according to the present invention includes the step of reacting a tris (fluoroaryl) borane with a compound represented by General Formula (5) in a molar ratio from 1:1.9 to 1:5 in a hydrocarbon solvent, and the tris (fluoroaryl) borane is represented by General Formula (4):

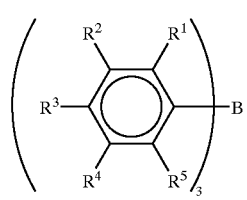

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom), and the compound is represented by General Formula (5):

$$R^6\text{—}MR^{14}(R^7)n \tag{5}$$

(where each of $R^6$, $R^7$, and $R^{14}$ independently represents one of a hydrogen atom and a hydrocarbon group, and M represents an atom belonging to Group 15 or Group 16 and n represents 0 or 1).

In the reaction of the tris(fluoroaryl) borane and the compound represented by General Formula (5) in the hydrocarbon solvent, it is preferable to set a using amount of the hydrocarbon solvent so that the concentration of the tris (fluoroaryl) borane ranges from 0.1 weight % to 80 weight %, and it is more preferable to set the using amount so that the concentration of the tris (fluoroaryl) borane ranges from 1 weight % to 30 weight %. It is preferable that a reaction temperature in the reaction ranges from 0° C. to 300° C., and it is more preferable that the reaction temperature ranges from 50° C. to 200° C.

In the reaction of the tris (fluoroaryl) borane and the compound (5) in the hydrocarbon solvent, it is preferable to set a using amount of the hydrocarbon solvent so that the concentration of the tris (fluoroaryl) borane ranges from 0.1 weight % to 80 weight %, and it is more preferable to set the using amount so that the concentration of the tris (fluoroaryl) borane ranges from 1 weight % to 30 weight %. It is preferable that a reaction temperature in the reaction ranges from 0° C. to 300° C., and it is more preferable that the reaction temperature ranges from 50° C. to 200° C.

The reaction mixture obtained by the method, that is, the solution containing the fluoroaryl borane derivative as an object, the bis (fluoroaryl) borane derivative, and the hydrocarbon solvent also contains the fluorobenzene as a byproduct so that the fluorobenzene is dissolved. When the fluoroaryl borane derivative and the bis (fluoroaryl) borane derivative are precipitated and filtrated respectively, it is possible to obtain the fluoroaryl borane derivative and the bis (fluoroaryl) borane derivative as solid respectively. Since the fluoroaryl borane derivative and the bis (fluoroaryl) borane derivative dissolve in the fluorobenzene, the fluorobenzene may be removed as required.

A method for purifying a fluoroaryl borane derivative and a bis (fluoroaryl) borane derivative according to the present invention includes the steps of: precipitating the fluoroaryl borane derivative from a solution containing the fluoroaryl borane derivative, the bis (fluoroaryl) borane derivative, and a hydrocarbon solvent; performing first filtration; precipitating the bis (fluoroaryl) borane derivative by cooling a filtrate that has been obtained by the first filtration; and performing second filtration. Further, a method for purifying a fluoroaryl borane derivative and a bis (fluoroaryl) borane derivative according to the present invention includes the steps of: concentrating a solution containing the fluoroaryl borane derivative, the bis (fluoroaryl) borane derivative, fluorobenzene, and a hydrocarbon solvent; precipitating the fluoroaryl borane derivative after removing the fluorobenzene from the solution; performing first filtration; precipitating the bis (fluoroaryl) borane derivative by cooling a filtrate that has been obtained by the first filtration; performing second filtration. Further, a method for purifying a bis (fluoroaryl) borane derivative according to the present invention includes the steps of: precipitating a fluoroaryl borane derivative after removing fluorobenzene from a solution containing the fluoroaryl borane derivative, the bis (fluoroaryl) borane derivative, the fluorobenzene, and a hydrocarbon solvent; performing first filtration; concentrating a filtrate that has been obtained by the first filtration; removing the fluorobenzene; precipitating the bis (fluoroaryl) borane derivative from the filtrate; and performing second filtration.

Furthermore, a method for purifying a fluoroaryl borane derivative and a bis (fluoroaryl) borane derivative according to the present invention includes the steps of: precipitating the fluoroaryl borane derivative after removing fluorobenzene from a solution containing the fluoroaryl borane derivative, the bis (fluoroaryl) borane derivative, the fluorobenzene, and a hydrocarbon solvent; performing first filtration; precipitating the bis (fluoroaryl) borane derivative by cooling a filtrate that has been obtained by the first filtration; and performing second filtration.

A fluoroaryl borane derivative that should be purified by the method for purifying according to the present invention is a compound represented by General Formula (1):

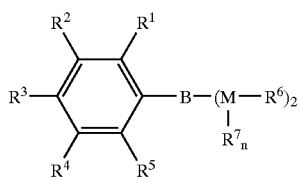
(1)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1).

In the general formula, specifically, the hydrocarbon group for the substitutional groups represented by $R^1$, $R^2$, $R^3$, $R^4$, and $R^5$ represents an aryl group such as a phenyl group, a straight or branched alkyl group containing 1 to 12 carbon atoms, a cyclic alkyl group containing 3 to 12 carbon atoms, a straight or branched alkenyl group containing 2 to 12 carbon atoms, and a cyclic alkenyl group containing 3 to 12 carbon atoms. Examples of the alkyl group are, specifically, a methyl group, an ethyl group, a propyl group, an isopropyl group, a butyl group, an isobutyl group, a t-butyl group, a pentyl group, an isopentyl group, a t-pentyl group, a hexyl group, an octyl group, a cyclopropyl group, a cyclobtyl group, a cyclopentyl group, a cyclohexyl group, and a methylcyclohexyl group. An example of the alkenyl group is, specifically, an allyl group.

Note that, the hydrocarbon group may further include a functional group including an atom that is inert to the purification (treatment) of the present invention, for example, a fluorine atom, a nitrogen atom, an oxygen atom, a sulfur atom, that is, an inert functional group. Examples of the functional group are a methoxy group, a methylthio group, an N,N-dimethylamino group, an o-anis group, a p-anis group, a trimethylsilyloxy group, a dimethyl-t-butylsilyloxy group, and a trifluoromethyl group.

In the general formula, the alkoxy group for the substitutional group represented by $R^1$, $R^2$, $R^3$, $R^4$, and $R^5$ is represented by General Formula (A):

—ORa (A)

(where Ra represents a hydrocarbon group). In the general formula, the hydrocarbon represented by Ra specifically represents an aryl group such as a phenyl group, a straight or branched alkyl group containing 1 to 12 carbon atoms, a cyclic alkyl group containing 3 to 12 carbon atoms, a straight or branched alkenyl group containing 2 to 12 carbon atoms, a cyclic alkenyl group containing 3 to 12 carbon atoms. Note that, the hydrocarbon group may further include a functional group including an atom that is inert to the purification of the present invention. Examples of the alkoxy group represented by General Formula (A) are, specifically, a methoxy group, an ethoxy group, an n-propoxy group, an isopropoxy group, an n butoxy group, an isobutoxy group, a sec-butoxy group, a t-butoxy group, a cyclohexyloxy group, an allyloxy group, and a phenoxy group.

In the general formula, an example of the hydrocarbon group represented by $R^6$ and $R^7$ is a substitutional group similar to the substitutional group of the hydrocarbon group represented by $R^1$, $R^2$, $R^3$, $R^4$, and $R^5$. In the general formula, a nitrogen atom or an oxygen atom is particularly preferable out of Group 5B (Group 15 in a long-period type) or Group 6B (Group 16 in a long-period type) of a substitutional group represented by M.

Thus, examples of the fluoroaryl borane derivative are, specifically, a p-fluorophenyl boronic acid, a 2,6-difluorophenyl boronic acid, a 2,4,6-trifluorophenyl boronic acid, a 2,3,5,6-tetrafluorophenyl boronic acid, a pentafluorophenyl boronic acid, and the like.

Note that, it is preferable that the purity of the fluoroaryl borane derivative that should be purified by the method of the present invention for purifying is not less than 90%. More preferably, the purity is not less than 95%. Still more preferably, the purity is not less than 98%. In this case, an amount of the bis (fluoroaryl) borane derivative contained as a byproduct is not more than 10%, more preferably not more than 5%, and still more preferably not more than 2%.

The bis (fluoroaryl) borane derivative that should be purified by the method for purifying according to the present invention is a compound represented by General Formula (2):

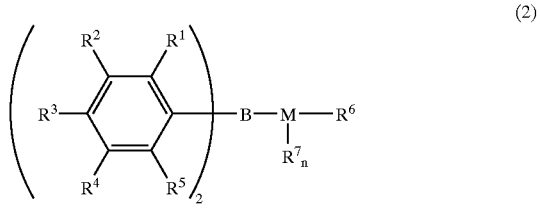
(2)

(where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an atom belonging to Group 5B or Group 6B, and n represents 0 or 1).

In the general formula, an example of the hydrocarbon group represented by $R^1$, $R^2$, $R^3$, $R^4$ and $R^5$ is, specifically, a substitutional group similar to the substitutional group of the hydrocarbon group and the alkoxy group that are represented by $R^1$, $R^2$, $R^3$, $R^4$, and $R^5$. In the general formula, an example of the hydrocarbon group represented by $R^6$ and $R^7$ is, specifically, a substitutional group similar to the substitutional group of the hydrocarbon group represented by $R^1$, $R^2$, $R^3$, $R^4$, and $R^5$. In the general formula, a nitrogen atom or an oxygen atom is particularly preferable out of Group 5B (Group 15 in a long-period type) or Group 6B (Group 16 in a long-period type) of a substitutional group represented by M.

Thus, examples of the bis (fluoroaryl) borane derivative are, specifically, a bis (p-fluorophenyl) borinic acid, a bis (2,6-difluorophenyl) borinic acid, a bis (2,4,6-trifluorophenyl) borinic acid, a bis (2,3,5,6-tetrafluorophenyl) borinic acid, a bis (pentafluorophenyl) borinic acid, and the like.

It is preferable that the purity of the bis (fluoroaryl) borane derivative that should be purified by the method of the present invention is not less than 95%. More preferably, the purity is not less than 98%. In this case, an amount of the fluoroaryl borane derivative which exists in the bis (fluoroaryl) borane derivative is not more than 2%, more preferably not more than 1%, and still more preferably not more than 0.8%.

The fluorobenzene that should be removed by the method according to the present invention for purifying is a compound represented by General Formula (3):

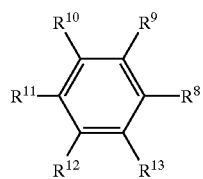

(3)

(where each of $R^9$, $R^{10}$, $R^{11}$, $R^{12}$, and $R^{13}$ independently represents one of a hydrogen atom, a fluorine atom, a hydrocarbon group, and an alkoxy group, and at least one of $R^9$, $R^{10}$, $R^{11}$, $R^{12}$, and $R^{13}$ represents the fluorine atom, and $R^8$ represents one of a hydrogen atom and a hydrocarbon group).

In the general formula, an example of the hydrocarbon group and the alkoxy group of the substitutional group represented by $R^9$, $R^{10}$, $R^{11}$, $R^{12}$, and $R^{13}$ is, specifically, a substitutional group similar to the substitutional group of the hydrocarbon group and the alkoxy group that are represented by $R^1$, $R^2$, $R^3$, $R^4$, and $R^5$. In the general formula, an example of the hydrocarbon group represented by $R^8$ is, specifically, a substitutional group similar to the substitutional group of the hydrocarbon group represented by $R^1$, $R^2$, $R^3$, $R^4$, and $R^5$.

Thus, examples of the fluorobenzene are, specifically, a fluorobenzene, a 2,6-difluorobenzene, a 2,4,6-trifluorobenzene, a 2,3,5,6-tetrafluorobenzene, a pentafluorobenzene, and the like.

Examples of the hydrocarbon solvent contained in the solution containing the fluoroaryl borane derivative and the bis (fluoroaryl) borane derivative are an aliphatic hydrocarbon solvent such as a saturated hydrocarbon solvent, unsaturated hydrocarbon solvent, and alicyclic hydrocarbon solvent, and an aromatic hydrocarbon solvent.

As the hydrocarbon solvent, the aliphatic hydrocarbon solvent is more preferable. Specifically, examples of the hydrocarbon solvent are 2,2-dimethylbutane, 2,3-dimethylbutane, 2,2,3-trimethylbutan, pentane, 2,2-dimethylpentane, 2,3-dimethylpentane, 2,4-dimethylpentane, 3,3-dimethylpentane, 2-methylpentane, 3-methylpentane, 2,2,4-trimethylpentane, 2,3,4-trimethylpentane, hexan, 2-methylhexane, 3-methylhexane, 2,2-dimehtylhexane, 2,4-dimethylhexane, 2,5-dimetylhexane, 3,4-dimethylhexane, heptane, 2-methylheptane, 3-methylheptane, 4-methylheptane, 2,3-dimethylheptane, octane, nonan, decane, undecane, dodecane, tridecane, pentene, hexen, heptene, octene, cyclopentane, methylcyclopentane, ethylcyclopentane, cyclohexane, methylcyclohexane, 1,2-dimethylcyclohexane, 1,3-dimethylcyclohexane, 1,4-dimethylcyclohexane, ethylcyclohexane, cycloheptane, cyclooctane, cyclopentene, and cyclohexene. One of those hydrocarbon solvents may be used solely or more than two of those hydrocarbon solvents may be appropriately mixed and used. Moreover, commercial hydrocarbon solvents such as IsoparC, IsoparE, and IsoparG (any of them are Registered Trademarks) supplied from Exxon Corp. may be used.

It is preferable that the hydrocarbon solvent is substantially an aliphatic hydrocarbon solvent. For example, bis (pentafluorophenyl) borinic acid, which is a bis (fluoroaryl) borane derivative, is relatively soluble to the aromatic hydrocarbon solvent such as toluene. Thus, bis (pentafluorophenyl) borinic acid has a low yield when isolation of bis (pentafluorophenyl) borinic acid is carried out by filtration after concentration of a reaction mixture, in case the aromatic hydrocarbon solvent is used as a solvent. Because of this, it is necessary to have a step of concentrating and drying up the reaction mixture by distilling off the solvent, in order to have a high yield for isolation of the bis (pentafluorophenyl) borinic acid.

On the other hand, the bis (fluoroaryl) borane derivative has a low solubility for the aliphatic hydrocarbon solvent. Thus, in case the hydrocarbon solvent is substantially an aliphatic hydrocarbon solvent, it is possible to have a high yield of the bis (fluoroaryl) borane derivative by the step of performing the filtration after cooling the reaction mixture.

Further, the foregoing hydrocarbon solvent may be a hydrocarbon solvent used to prepare the fluoroaryl borane derivative or the bis (fluoroaryl) borane derivative by reacting the tris (fluoroaryl) borane represented by General Formula (4) with the compound represented by General Formula (5).

Note that, in the present invention, the wording "the hydrocarbon solvent is substantially an aliphatic hydrocarbon solvent" means that a ratio of the aliphatic hydrocarbon solvent in the hydrocarbon solvent is within a range of 80% by weight to 100% by weight, and more preferably within a range of 95% by weight to 100% by weight.

In the method for purifying according to the present invention, the solution (hereinbelow, sometimes referred to merely as solution A) containing the fluoroaryl borane derivative, the bis (fluoroaryl) borane derivative, and the hydrocarbon solvent is subjected to the first filtration after precipitating the fluoroaryl borane derivative at temperature at which the fluoroaryl borane derivative is precipitated, and the filtrate obtained by the first filtration is cooled after isolating the fluoroaryl borane derivative as a precipitated deposit, and the cooled filtrate is subjected to the second filtration after precipitating the bis (fluoroaryl) borane derivative, and the bis (fluoroaryl) borane derivative is isolated as a solid, so that the fluoroaryl borane derivative and the bis (fluoroaryl) borane derivative are purified.

The temperature at which the fluoroaryl borane derivative is separated from the solution A is set so that the fluoroaryl borane derivative is sufficiently precipitated, and it is more preferable that the temperature is set so that the bis (fluoroaryl) borane derivative is not precipitated, or the bis (fluoroaryl) borane derivative is hardly precipitated. Specifically, it is preferable that the temperature is within a range of −30° C. to 300° C., and more preferably within a range of 0° C. to 200° C.

The fluoroaryl borane derivative may be isolated from the solution A as follows: after the fluoroaryl borane derivative is precipitated from the solution A by distilling off the hydrocarbon solvent as required, the first filtration is performed so as to isolate the fluoroaryl borane derivative from the solution A.

As a method for distilling off the hydrocarbon solvent, specifically, the following methods may be employed: the solution A is heated under an ordinary pressure (atmospheric pressure), or the solution A is heated under a reduced pressure or a pressurization condition. In this way, the method for distilling off the hydrocarbon solvent is not particularly limited. Further, the heating temperature is set to be more than each boiling temperature of the hydrocarbon solvent at each pressure.

Note that, the hydrocarbon solvent in the filtrate obtained by the first filtration may be removed as required before the bis (fluoroaryl) borane derivative is precipitated by cooling the filtrate. That is, the bis (fluoroaryl) borane derivative may be isolated as a solid as follows: after the hydrocarbon solvent in the filtrate obtained by the first filtration is distilled off, the filtrate in which the hydrocarbon solvent has been partially distilled off is cooled so as to precipitate the bis (fluoroaryl) borane derivative, and the bis (fluoroaryl) borane derivative is isolated as a solid by performing the second filtration.

The temperature at which the filtrate is cooled so as to precipitate the bis (fluoroaryl) borane derivative may be set so that the bis (fluoroaryl) borane derivative is sufficiently precipitated. Specifically, the temperature preferably is in a range from −50° C. to 200° C., more preferably from −30° C. to 100° C. Time taken to cool the filtrate may be suitably set according to an amount etc. of the reaction mixture.

Note that, the following step may be employed: the filtrate obtained by the second filtration is further concentrated and the bis (fluoroaryl) borane derivative is precipitated so as to filtrate the separated bis (fluoroaryl) borane derivative, so that the bis (fluoroaryl) borane derivative contained in the filtrate is isolated. The concentration of the filtrate is performed by removing the hydrocarbon solvent from the filtrate. Specifically, the concentration of the filtrate can be performed in the same manner as in distilling off the hydrocarbon solvent from the solution A.

Note that, the filtrate obtained by the second filtration, or a filtrate obtained by concentrating that filtrate so as to remove the precipitated bis (fluoroaryl) borane derivative may be reused (recycled) as a hydrocarbon solvent.

By performing the foregoing steps, it is possible to precipitate the fluoroaryl borane derivative as a solid. The fluoroaryl borane derivative can be isolated by performing the first filtration. Further, by cooling the filtrate after the first filtration, the bis (fluoroaryl) borane derivative can be precipitated as a solid. By performing the second filtration, the bis (fluoroaryl) borane derivative can be isolated. That is, it is possible to obtain the high-purity fluoroaryl borane derivative and bis (fluoroaryl) borane derivative containing no impurity with ease and at a low cost.

A method according to the present invention for purifying a fluoroaryl borane derivative and a bis (fluoroaryl) borane derivative includes the steps of: concentrating a solution (hereinbelow, sometimes referred to merely as solution B) containing the fluoroaryl borane derivative, the bis (fluoroaryl) borane derivative, fluorobenzene, and a hydrocarbon solvent; removing the fluorobenzene from the solution; precipitating the fluoroaryl borane derivative at temperature at which the fluoroaryl borane derivative is precipitated; performing first filtration; isolating the fluoroaryl borane derivative; cooling a filtrate that has been obtained by the first filtration; precipitating the bis (fluoroaryl) borane derivative; performing second filtration; and isolating the bis (fluoroaryl) borane derivative as a solid.

It is possible to concentrate the solution B by distilling off the fluorobenzene and/or the hydrocarbon solvent from the solution B. As a method for distilling off the hydrocarbon solvent, specifically, the following methods may be employed: the solution B is heated under an ordinary pressure (atmospheric pressure), or the solution B is heated under a reduced pressure or a pressurization condition. In this way, the method is not particularly limited. Further, the heating temperature is set to be more than each boiling temperature of the fluorobenzene at each pressure. Time taken to concentrate the reaction mixture may be suitably set according to an amount etc. of the reaction mixture.

The concentrated solution obtained by concentrating the solution B substantially contains the fluoroaryl borane derivative, the bis (fluoroaryl) borane derivative, and the hydrocarbon solvent.

Next, the first filtration is performed after precipitating the fluoroaryl borane derivative from the concentrated solution, so that the fluoroaryl borane derivative can be isolated and purified. The second filtration is performed after the filtrate is further cooled so as to precipitate the bis (fluoroaryl) borane derivative, so that the bis (fluoroaryl) borane derivative can be isolated as a solid and can be purified. Note that, the foregoing first and second filtration are performed as in the filtration of the solution A.

Note that, before the filtrate obtained by the first filtration is cooled so as to precipitate the bis (fluoroaryl) borane derivative, the hydrocarbon solvent in the filtrate may be distilled off as required. That is, the following step may be employed: after distilling off the hydrocarbon solvent in the filtrate obtained by the first filtration, the filtrate with the hydrocarbon solvent partially distilled off is cooled, and the bis (fluoroaryl) borane derivative is precipitated so as to perform the second filtration, so that the bis (fluoroaryl) borane derivative is isolated as a solid.

Further, the following step may be employed: the filtrate obtained by the second filtrate is further concentrated, and the bis (fluoroaryl) borane derivative is precipitated, and the precipitated bis (fluoroaryl) borane derivative is filtrated, so that the bis (fluoroaryl) borane derivative contained in the filtrate is isolated. The concentration of the filtrate is performed by removing the hydrocarbon solvent from the filtrate. Specifically, the concentration can be performed in the same manner as in distilling off the hydrocarbon solvent from the solution A.

Note that, the filtrate obtained by the second filtration, or a filtrate obtained by concentrating that filtrate so as to remove the precipitated bis (fluoroaryl) borane derivative may be reused (recycled) as a hydrocarbon solvent.

By performing the foregoing steps, after distilling off the fluorobenzene from the solution, it is possible to precipitate the fluoroaryl borane derivative and to isolate the fluoroaryl borane derivative so as to perform the first filtration. Further, by cooling the filtrate that has been obtained by the first filtration, the bis (fluoroaryl) borane derivative can be isolated as a solid. That is, it is possible to obtain the high-purity fluoroaryl borane derivative and bis (fluoroaryl) borane derivative containing no impurity with ease and at a low cost.

A method according to the present invention for purifying a fluoroaryl borane derivative and a bis (fluoroaryl) borane derivative includes the steps of: precipitating the fluoroaryl borane derivative at temperature at which the fluoroaryl borane derivative is precipitated from a solution (solution B) containing the fluoroaryl borane derivative, the bis (fluoroaryl) borane derivative, fluorobenzene, and a hydrocarbon solvent; performing first filtration; isolating the fluoroaryl borane derivative; concentrating a filtrate that has been obtained by the first filtration; removing the fluorobenzene from the filtrate; performing second filtration; isolating the bis (fluoroaryl) borane derivative precipitated in the filtrate that has been concentrated.

The first filtration is performed after the fluoroaryl borane derivative has been precipitated, so that it is possible to isolate the fluoroaryl borane derivative from the solution B. Note that, the first filtration is performed specifically in the same manner as in the solution A.

By concentrating the filtrate obtained by the first filtration, it is possible to remove the fluorobenzene from the filtrate as distillate. Note that, the step for concentrating the filtrate is performed specifically in the same manner as in the solution B.

The concentration of the bis (fluoroaryl) borane derivative in the filtrate becomes high by concentrating the filtrate obtained by the first filtration and the concentration exceeds the solubility, so that a crystal is precipitated. Further, to precipitate the bis (fluoroaryl) borane derivative, the concentrated filtrate may be cooled. The material precipitated from the filtrate is subjected to the second filtration, so that it is possible to readily isolate the bis (fluoroaryl) borane derivative as a solid. Note that, the second filtration is performed specifically in the same manner as in the solution A.

Further, the following step may be employed: the filtrate obtained by the second filtration is further concentrated, and the bis (fluoroaryl) borane derivative is precipitated, and the precipitation of bis (fluoroaryl) borane derivative is filtrated, so that the bis (fluoroaryl) borane derivative contained in the filtrate is isolated. The concentration of the filtrate is performed by removing the hydrocarbon solvent from the filtrate. Specifically, the concentration is performed in the same manner as in distilling off the hydrocarbon solvent from the solution A.

Note that, the filtrate obtained by the second filtration, or a filtrate obtained by concentrating that filtrate so as to remove the precipitated bis (fluoroaryl) borane derivative may be reused (recycled) as hydrocarbon solvent.

By performing the foregoing steps, it is possible to precipitate the fluoroaryl borane derivative and to isolate the fluoroaryl borane derivative by performing the first filtration. Further, after concentrating the filtrate that remains after the first filtration so as to distill off the fluorobenzene, the bis (fluoroaryl) borane derivative precipitated as a solid can be separated by the second filtration. That is, it is possible to obtain the high-purity fluoroaryl borane derivative and bis (fluoroaryl) borane derivative containing no impurity with ease and at a low cost.

As described above, in the method of the present invention for purifying, since a precipitating condition, a condition for filtrating, and a heating condition with respect to a reaction mixture are employed in a specific order, it is possible to isolate the fluoroaryl borane derivative and the bis (fluoroaryl) borane derivative respectively. Further, if a method for producing either the fluoroaryl borane derivative or the bis (fluoroaryl) borane derivative efficiently is employed, it is possible to produce either the fluoroaryl borane derivative or the bis (fluoroaryl) borane derivative as desired. As a result, it is possible to obtain the high-purity fluoroaryl borane and bis (fluoroaryl) borane derivative more easily.

Further, since the method of the present invention for purifying is completely different from prior arts in the purifying steps, boroxine generated in prior arts is not generated. Consequently, it is possible to obtain the high-purity fluoroaryl borane derivative and bis (fluoroaryl) borane derivative more easily.

BEST MODE FOR CARRYING OUT THE INVENTION

The present invention is explained in more detail below referring to examples. However, the present invention is not limited to those. Note that NMR (Nuclear Magnetic Resonance) spectrum data was measured in the examples in such a manner that tetramethylsilane (TMS) was a standard substance for $^1$H-NMR spectrum data, while trifluoro acetic acid was a standard substance for $^{19}$F-NMR spectrum data so that signals of the standard substances were assumed to be 0 ppm. Note that, the following EXAMPLEs 1 and 2 are examples in which much bis (fluoroaryl) borane derivative is generated, and EXAMPLE 3 is an example in which much fluoroaryl borane derivative is generated.

EXAMPLE 1

2064.22 g of IsoparE (supplied from Exxon Corp.) solution containing 56.766 g (0.1109 mol) of tris (pentafluorophenyl) borane as tris (fluoroaryl) borane and 2.020 g (0.1121 mol) of water were added into a reaction vessel equipped with a reflux condenser, a thermometer, a dropping funnel and a stirrer.

Next, the content of the reaction vessel was heated to 100° C. with stirring. Reaction was carried out for 4 hours at 100° C. A part of the reaction mixture obtained from the reaction for 4 hours was analyzed by $^{19}$F-NMR. It showed that the reaction mixture contained 50.60 mol % of bis (pentafluorophenyl) borinic acid, 0.87 mol % of pentafluorophenyl boronic acid, 48.40 mol % of pentafluorobenzene, and 0.10 mol % of tris (pentafluorophenyl) borane.

A distillation apparatus was used instead of the reflux condenser provided on the reactor so as to perform reduced pressure distillation under a condition of 6.7 kPa (50 mmHg). At this time, an amount of distillate was 1731.54 g.

A residue (concentrated solution) obtained by the reduced pressure distillation was kept at 60° C., and the precipitation, namely, the pentafluorophenyl boronic acid corresponding to the fluoroaryl borane derivative was precipitated. Thereafter, the distillate was filtrated so as to isolate the pentafluorophenyl boronic acid. Further, the filtrate obtained by filtrating the distillate was cooled down to 15° C., and the precipitation, namely, the bis (pentafluorophenyl) borinic acid corresponding to the bis (fluoroaryl) borane derivative was precipitated. Thereafter, a cake obtained by filtrating the distillate was washed with 40 ml of hexane so as to dry the cake at 70° C. under a reduced pressure. A weight of the dried cake was 29.987 g. The cake was analyzed by $^{19}$F-NMR. It showed that the cake contained 0% of the pentafluorophenyl boronic acid and 100 weight % of bis (pentafluorophenyl) borinic acid.

As described above, according to the method of the present invention for purifying, it is possible to obtain the fluoroaryl borane derivative and the bis (fluoroaryl) borane derivative from the solution containing pentafluorophenyl boronic acid which functions as the fluoroaryl borane derivative, bis (pentafluorophenyl) borinic acid which functions as the bis (fluoroaryl) borane derivative, pentafluorobenzene which functions as the fluorobenzene, and IsoparE which functions as the hydrocarbon solvent, with ease and at a low cost.

Note that, NMR spectrum data of the bis (pentafluorophenyl) borinic acid in the cake was as follows: $^{19}$F-NMR (benzene—d6, δ); −57.6, −72.2, −85.6 ppm

EXAMPLE 2

809.56 g of IsoparE (supplied from Exxon Corp.) solution of IsoparE containing 22.263 g (0.0435 mol) of tris (pentafluorophenyl) borane as tris (fluoroaryl) borane and 0.941 g (0.0522 mol) of water were added into a reaction vessel equipped with a reflux condenser, a thermometer, a dropping funnel and a stirrer.

Next, the content of the reaction vessel was heated to 100° C. with stirring. Reaction was carried out for 4 hours at 100° C. A part of the reaction mixture obtained from the reaction for 4 hours was analyzed by $^{19}$F-NMR. It showed that the reaction mixture contained 49.3 mol % of bis (pentafluorophenyl) borinic acid, 1.1 mol % of pentafluorophenyl boronic acid, 49.4 mol % of pentafluorobenzene, and 0.2 mol % of tris (pentafluorophenyl) borane.

A distillation apparatus was used instead of the reflux condenser provided on the reactor so as to perform reduced pressure distillation under a condition of 8.7 kPa (65 mmHg). At this time, an amount of distillate was 703.86 g.

A residue (concentrated solution) obtained by the vacuum concentration was kept at 65° C., and the precipitation, namely, the pentafluorophenyl boronic acid corresponding to the fluoroaryl borane derivative was precipitated. Thereafter, the distillate was filtrated so as to isolate the pentafluorophenyl boronic acid. Further, the filtrate obtained by filtrating the distillate was cooled down to 7° C., and the precipitated material, namely, the bis (pentafluorophenyl) borinic acid corresponding to the bis (fluoroaryl) borane derivative was precipitated. Thereafter, a cake obtained by filtrating the distillate was washed with 20 ml of hexane so as to dry the cake under a reduced pressure. A weight of the dried cake was 12.540 g. The cake was analyzed by $^{19}$F-NMR. It showed that the cake contained 98.6 weight % of the bis (pentafluorophenyl) borinic acid, 0.6 weight % of the pentafluorophenyl boronic acid, and 0.8 weight % of pentafluoro benzene.

As described above, according to the method of the present invention for purifying, it is possible to obtain the fluoroaryl borane derivative and the bis (fluoroaryl) borane derivative from the solution containing bis (pentafluorophenyl) borinic acid which functions as the bis (fluoroaryl) borane derivative, pentafluorophenyl boronic acid which functions as the fluoroaryl borane derivative, pentafluorobenzene which functions as the fluorobenzene, and IsoparE which functions as the hydrocarbon solvent, with ease and at a low cost.

Note that, NMR spectrum data of the pentafluorophenyl boronic acid in the cake was as follows: $^{19}$F-NMR (benzene—d6, δ); −57.3, −75.1, −86.4 ppm

EXAMPLE 3

1139.76 g of an ethylcyclohexane solution containing 41.695 g (0.0814 mol) of tris (pentafluorophenyl) borane as tris (fluoroaryl) borane and 4.404 g (0.2444 mol) of water were added into a reaction vessel equipped with a reflux condenser, a thermometer, a dropping funnel and a stirrer.

Next, the content of the reaction vessel was heated to 100° C. with stirring. Reaction was carried out for 18 hours at A distillation apparatus was used instead of the reflux cooler provided on the reactor so as to perform vacuum concentration under a condition of 6.7 kPa (50 mmHg). At this time, an amount of distillate was 653.66 g.

A residue (concentrated solution) obtained by the vacuum concentration was kept at 60° C., and the precipitated material, namely, the pentafluorophenyl boronic acid corresponding to the fluoroaryl borane derivative was precipitated. Thereafter, the distillate was filtrated so as to isolate the pentafluorophenyl boronic acid. A cake obtained by filtrating the distillate was washed with 100 ml of hexane so as to dry the cake at 40° C. under a reduced pressure. A weight of the dried cake was 8.5582 g. The cake was analyzed by $^{19}$F-NMR. It showed that the cake contained 100 weight % of the pentafluorophenyl boronic acid.

As described above, according to the method of the present invention for purifying, it is possible to obtain the fluoroaryl borane derivative from the solution containing pentafluorophenyl boronic acid which functions as the fluoroaryl borane derivative, bis (pentafluorophenyl) borinic acid which functions as the bis (fluoroaryl) borane derivative, pentafluorobenzene which functions as the benzene fluoride, and ethylcyclohexane which functions as the hydrocarbon solvent, with ease and at a low cost.

Note that, NMR spectrum data of the pentafluorophenyl boronic acid in the cake was as follows: $^{19}$F-NMR (acetone—d6, δ); −57.7, −79.9, −86.6 ppm Further, MS (mass spectrum) data of the pentafluorophenyl boronic acid in the cake was as follows: MASS (M/Z); 212

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

INDUSTRIAL APPLICABILITY

A method of the present invention for purifying a fluoroaryl borane derivative and a bis (fluoroaryl) borane derivative, as described above, includes the steps of: precipitating the fluoroaryl borane derivative from a solution containing the fluoroaryl borane derivative, the bis (fluoroaryl) borane derivative, and a hydrocarbon solvent; performing first filtration so that the fluoroaryl borane derivative is isolated; cooling a filtrate that has been obtained by the first filtration; precipitating the bis (fluoroaryl) borane derivative; and performing second filtration.

A method of the present invention for purifying a fluoroaryl borane derivative and a bis (fluoroaryl) borane derivative, as described above, includes the steps of: precipitating the fluoroaryl borane derivative from a solution containing the fluoroaryl borane derivative, the bis (fluoroaryl) borane derivative, fluorobenzene, and a hydrocarbon solvent; performing first filtration so that the fluoroaryl borane derivative is isolated as a solid; precipitating the bis (fluoroaryl) borane derivative from a filtrate that has been obtained by the first filtration; and performing second filtration.

A method of the present invention for purifying a fluoroaryl borane derivative and a bis (fluoroaryl) borane derivative, as described above, includes the steps of: concentrating a solution containing the bis (fluoroaryl) borane derivative, the fluorobenzene, and a hydrocarbon solvent so as to remove fluorobenzene from the solution; precipitating the fluoroaryl borane derivative; performing first filtrate so that the fluoraryl borane derivative is isolated; cooling a filtrate that has been obtained by the first filtration; precipitating the bis (fluoroaryl) borane derivative; and performing second filtration.

A method of the present invention for purifying a fluoroaryl borane derivative and a bis (fluoroaryl) borane derivative, as described above, includes the steps of: precipitating the fluoroaryl borane derivative from a solution containing the fluoroaryl borane derivative, the bis (fluoroaryl) borane derivative, fluorobenzene, and a hydrocarbon solvent; performing first filtration so that the fluoroaryl borane derivative is isolated; concentrating a filtrate that has been obtained by the first filtration so as to remove the fluorobenzene from the filtrate; precipitating the bis (fluoroaryl) borane derivative from the filtrate; and performing second filtration.

A method of the present invention for purifying a fluoroaryl borane derivative and a bis (fluoroaryl) borane derivative, as described above, is arranged so that: a solution containing the fluoroaryl borane derivative and the bis (fluoroaryl) borane derivative is obtained by reacting tris (fluoroaryl) borane with a compound represented by General Formula (5) in a molar ratio from 1:0.9 to 1:1.1 in a hydrocarbon solvent.

A method of the present invention for purifying a fluoroaryl borane derivative and a bis (fluoroaryl) borane derivative, as described above, is arranged so that: a solution containing the fluoroaryl borane derivative and the bis (fluoroaryl) borane derivative is obtained by reacting tris (fluoroaryl) borane with a compound represented by General Formula (5) in a molar ratio from 1:1.9 to 1:5 in a hydrocarbon solvent.

A method of the present invention for purifying a fluoroaryl borane derivative and a bis (fluoroaryl) borane derivative, as described above, is arranged so that: the hydrocarbon solvent is substantially an aliphatic hydrocarbon solvent.

Therefore, since the fluorobenzene can be removed by performing simple operations (steps), it is possible to purify the fluoroaryl borane derivative and the bis (fluoroaryl) borane derivative with ease and at a low cost. That is, it is possible to obtain the highly-purified fluoroaryl borane derivative and bis (fluoroaryl) borane derivative containing no impurity with ease and at a low cost.

A fluoroaryl borane derivative of the present invention, as described above, is arranged to contain a bis (fluoroaryl) borane derivative so that the content of the bis (fluoroaryl) borane derivative is not more than 1 weight %.

A fluoroaryl borane derivative of the present invention is arranged to have purity of not less than 90%.

A bis (fluoroaryl) borane derivative of the present invention, as described above, is arranged to contain a fluoroaryl borane derivative so that the content of the fluoroaryl borane derivative is not more than 1%.

A bis (fluoroaryl) borane derivative of the present invention is arranged to have purity of not less than 95%.

A method of the present invention for purifying a fluoroaryl borane derivative, as described above, is arranged to react tris (fluoroaryl) borane with a compound represented by General Formula (5) in a molar ratio from 1:1.9 to 1:1.5 in a hydrocarbon solvent.

A fluoroaryl borane derivative obtained by a method of the present invention for producing a fluoroaryl borane derivative, as described above, is arranged to have purity of not less than 90%.

Therefore, it is possible to industrially use a fluoroaryl borane derivative and a bis (fluoroaryl) borane derivative as catalysts and the like.

What is claimed is:

1. A method for purifying a fluoroaryl borane derivative and a bis (fluoroaryl) borane derivative comprising the steps of:

precipitating the fluoroaryl borane derivative from a solution containing the fluoroaryl borane derivative, the bis (fluoroaryl) borane derivative, and a hydrocarbon solvent;

performing first filtration so that the fluoroaryl borane derivative is isolated;

precipitating the bis (fluoroaryl) borane derivative from a filtrate, that has been obtained by the first filtration, after performing the first filtration; and performing second filtration so that the bis (fluoroaryl) boron derivative is isolated, said fluoroaryl borane derivative being represented by Formula (1):

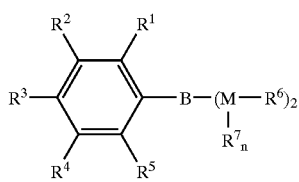

(1)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents a hydrogen atom or a hydrocarbon group, and M represents an oxygen atom and n represents 0, said bis (fluoroaryl) borane derivative being represented by Formula (2):

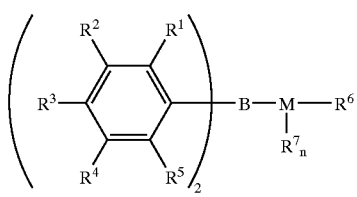

(2)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, and M represents an oxygen atom and n represents 0.

2. A method for purifying a fluoroaryl borane derivative and a bis (fluoroaryl) borane derivative comprising the steps of:

precipitating the fluoroaryl borane derivative from a solution containing the fluoroaryl borane derivative, the bis (fluoroaryl) borane derivative, fluorobenzene, and a hydrocarbon solvent;

performing first filtration so that the fluoroaryl borane derivative is isolated as a solid;

precipitating the bis (fluoroaryl) borane derivative from a filtrate, that has been obtained by the first filtration, after performing the first filtration; and performing second filtration so that the bis (fluoroaryl) borane derivative is isolated as a solid, said fluoroaryl borane derivative being represented by Formula (1):

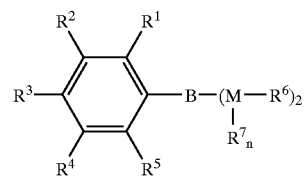

(1)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, and M represents an oxygen atom, and n represents 0, or said bis (fluoroaryl) borane derivative being represented by Formula (2):

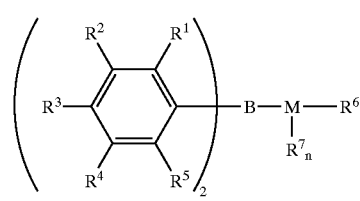

(2)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, and M represents an oxygen atom and n represents 0.

3. A method for purifying a fluoroaryl borane derivative and a bis (fluoroaryl) borane derivative comprising the steps of:

precipitating the fluoroaryl borane derivative from a solution, containing the fluoroaryl borane derivative, the bis (fluoroaryl) borane derivative, and a hydrocarbon solvent, that has been obtained by removing fluorobenzene from a solution containing the fluoroaryl borane derivative, the bis (fluoroaryl) borane derivative, the fluorobenzene, and the hydrocarbon solvent;

performing first filtration so that the fluoroaryl borane derivative is isolated as a solid;

precipitating the bis (fluoroaryl) borane derivative from a filtrate, that has been obtained by the first filtration, after performing the first filtration; and performing second filtration so that the bis (fluoroaryl) borane derivative is isolated as a solid, said fluoroaryl borane derivative being represented by Formula (1):

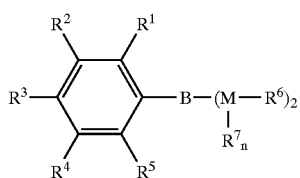

(1)

where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an oxygen atom and n represents 0, or said bis (fluoroaryl) borane derivative being represented by Formula (2):

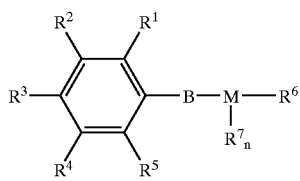

(2)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, and M represents an oxyRen atom and n represents 0.

4. A method for purifying a fluoroaryl borane derivative and a bis (fluoroaryl) borane derivative comprising the steps of:

precipitating the fluoroaryl borane derivative from a solution containing the fluoroaryl borane derivative, the bis (fluoroaryl) borane derivative, fluorobenzene, and a hydrocarbon solvent;

performing first filtration so that the fluoroaryl borane derivative is isolated as a solid;

precipitating the bis (fluoroaryl) borane derivative from a hydrocarbon solution, that has been obtained by removing the fluorobenzene, after performing the first filtration; and performing second filtration so that the his (fluoroaryl) borane derivative is isolated as a solid, said fluoroaryl borane derivative being represented by Formula (1):

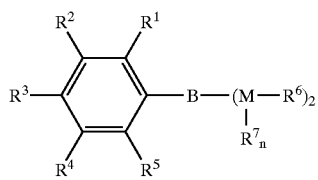

(1)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, and M represents an oxygen atom and n represents 0, or said bis (fluoroaryl) borane derivative being represented by Formula (2):

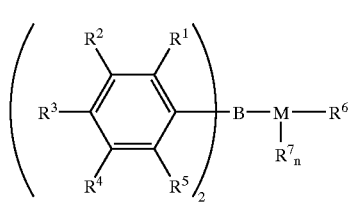

(2)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ represents one of a hydrogen atom and a hydrocarbon group, and M represents an oxygen atom and n represents 0.

5. The method as set forth in claim 1, wherein the hydrocarbon solvent is substantially an aliphatic hydrocarbon solvent.

* * * * *

UNITED STATES PATENT AND TRADEMARK OFFICE
CERTIFICATE OF CORRECTION

PATENT NO. : 6,818,785 B2
APPLICATION NO. : 10/220635
DATED : November 16, 2004
INVENTOR(S) : I. Ikeno et al.

It is certified that error appears in the above-identified patent and that said Letters Patent is hereby corrected as shown below:

Claim 3 should read

--3. A method for purifying a fluoroaryl borane derivative and a bis (fluoroaryl) borane derivative comprising the steps of:

precipitating the fluoroaryl borane derivative from a solution, containing the fluoroaryl borane derivative, the bis (fluoroaryl) borane derivative, and a hydrocarbon solvent, that has been obtained by removing fluorobenzene from a solution containing the fluoroaryl borane derivative, the bis (fluoroaryl) borane derivative, the fluorobenzene, and the hydrocarbon solvent;

performing first filtration so that the fluoroaryl borane derivative is isolated as a solid;

precipitating the bis (fluoroaryl) borane derivative from a filtrate, that has been obtained by the first filtration, after performing the first filtration; and performing second filtration so that the bis (fluoroaryl) borane derivative is isolated as a solid, said fluoroaryl borane derivative being represented by Formula (1):

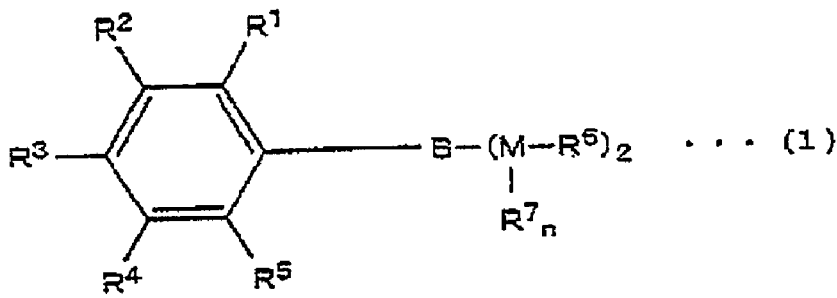

UNITED STATES PATENT AND TRADEMARK OFFICE
CERTIFICATE OF CORRECTION

| | |
|---|---|
| PATENT NO. | : 6,818,785 B2 |
| APPLICATION NO. | : 10/220635 |
| DATED | : November 16, 2004 |
| INVENTOR(S) | : I. Ikeno et al. |

It is certified that error appears in the above-identified patent and that said Letters Patent is hereby corrected as shown below:

Claim 3 should read (cont'd)

where each of $R^1$, $R^2$, $R^3$, $R^4$, and $R^5$ independently represents one of a hydrogen atom, a fluorine atom, a hydrocarbon group, and an alkoxy group, and at least one of $R^1$, $R^2$, $R^3$, $R^4$, and $R^5$ represents the fluorine atom, and each of $R^6$ and $R^7$ independently represents one of a hydrogen atom and a hydrocarbon group, and M represents an oxygen atom and n represents 0, or said bis (fluoroaryl) borane derivative being represented by Formula (2):

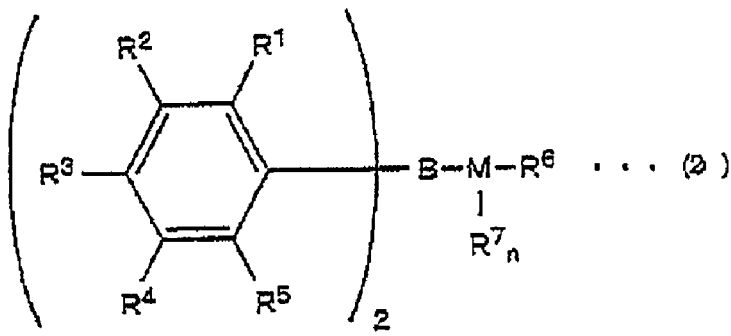

UNITED STATES PATENT AND TRADEMARK OFFICE
CERTIFICATE OF CORRECTION

PATENT NO. : 6,818,785 B2
APPLICATION NO. : 10/220635
DATED : November 16, 2004
INVENTOR(S) : I. Ikeno et al.

It is certified that error appears in the above-identified patent and that said Letters Patent is hereby corrected as shown below:

Claim 3 should read (cont'd)

where each of $R^1$, $R^2$, $R^3$, $R^4$ and $R^5$ independently represents one of a hydrogen atom, a fluorine atom, a hydrocarbon group, and an alkoxy group, provided at least one of $R^1$, $R^2$, $R^3$, $R^4$ and $R^5$ is a fluorine atom, and each of $R^6$ and $R^7$ independently represents one of a hydrogen atom and a hydrocarbon group, and M represents an oxygen atom and n represents O.--

Signed and Sealed this

Sixth Day of March, 2007

JON W. DUDAS
*Director of the United States Patent and Trademark Office*